United States Patent
Schächtele et al.

(10) Patent No.: US 10,661,075 B2
(45) Date of Patent: May 26, 2020

(54) ELECTRO-ACOUSTIC IMPLANT

(71) Applicant: Vibrosonic GmbH, Mannheim (DE)

(72) Inventors: Jonathan Schächtele, Mannheim (DE); Dominik Kaltenbacher, Mannheim (DE)

(73) Assignee: Vibrosonic GmbH, Mannheim (DE)

( * ) Notice: Subject to any disclaimer, the term of this patent is extended or adjusted under 35 U.S.C. 154(b) by 222 days.

(21) Appl. No.: 15/547,944

(22) PCT Filed: Jan. 27, 2016

(86) PCT No.: PCT/EP2016/051713
§ 371 (c)(1),
(2) Date: Aug. 1, 2017

(87) PCT Pub. No.: WO2016/124465
PCT Pub. Date: Aug. 11, 2016

(65) Prior Publication Data
US 2018/0021568 A1 Jan. 25, 2018

(30) Foreign Application Priority Data
Feb. 2, 2015 (DE) .................. 10 2015 101 482.3

(51) Int. Cl.
*A61N 1/05* (2006.01)
*A61N 1/36* (2006.01)
*H04R 25/00* (2006.01)

(52) U.S. Cl.
CPC ....... *A61N 1/0541* (2013.01); *A61N 1/36036* (2017.08); *A61N 1/36038* (2017.08); *H04R 25/48* (2013.01)

(58) Field of Classification Search
CPC .............. A61N 1/0541; A61N 1/36038; A61N 1/36036; H04R 25/48
See application file for complete search history.

(56) References Cited

U.S. PATENT DOCUMENTS

| 6,190,305 | B1 | 2/2001 | Ball et al. |
| 2004/0133250 | A1* | 7/2004 | Ball ...................... A61N 1/0541 607/57 |

(Continued)

FOREIGN PATENT DOCUMENTS

WO    WO-2016048936 A1    3/2016

OTHER PUBLICATIONS

"European Application Serial No. 16 701 930.6, Office Action dated Nov. 6, 2018", w/ machine translation, (Nov. 6, 2018), 12 pgs.

(Continued)

*Primary Examiner* — Catherine M Voorhees
*Assistant Examiner* — Roland Dinga
(74) *Attorney, Agent, or Firm* — Schwegman Lundberg & Woessner, P.A.

(57) ABSTRACT

An electro-acoustic implant comprising an elongate electrode carrier having a plurality of stimulation electrodes that can be introduced into a cochlea and comprising a flat sound transducer that is excitable to vibrate at least regionally by applying a voltage, with the sound transducer being configured such that it is arrangeable in, on and/or in front of a round window or an oval window or a surgically created third window of an ear and/or in a round window niche of an ear, covering the corresponding window at least partially or completely, such that vibrations of the sound transducer effect sound vibrations through the corresponding window, with the elongate electrode carrier extending through a surface of the flat sound transducer that extends, when the sound transducer is arranged in front of the corresponding window, at least partially over the corresponding window.

18 Claims, 11 Drawing Sheets

(56) References Cited

U.S. PATENT DOCUMENTS

Figure 1:
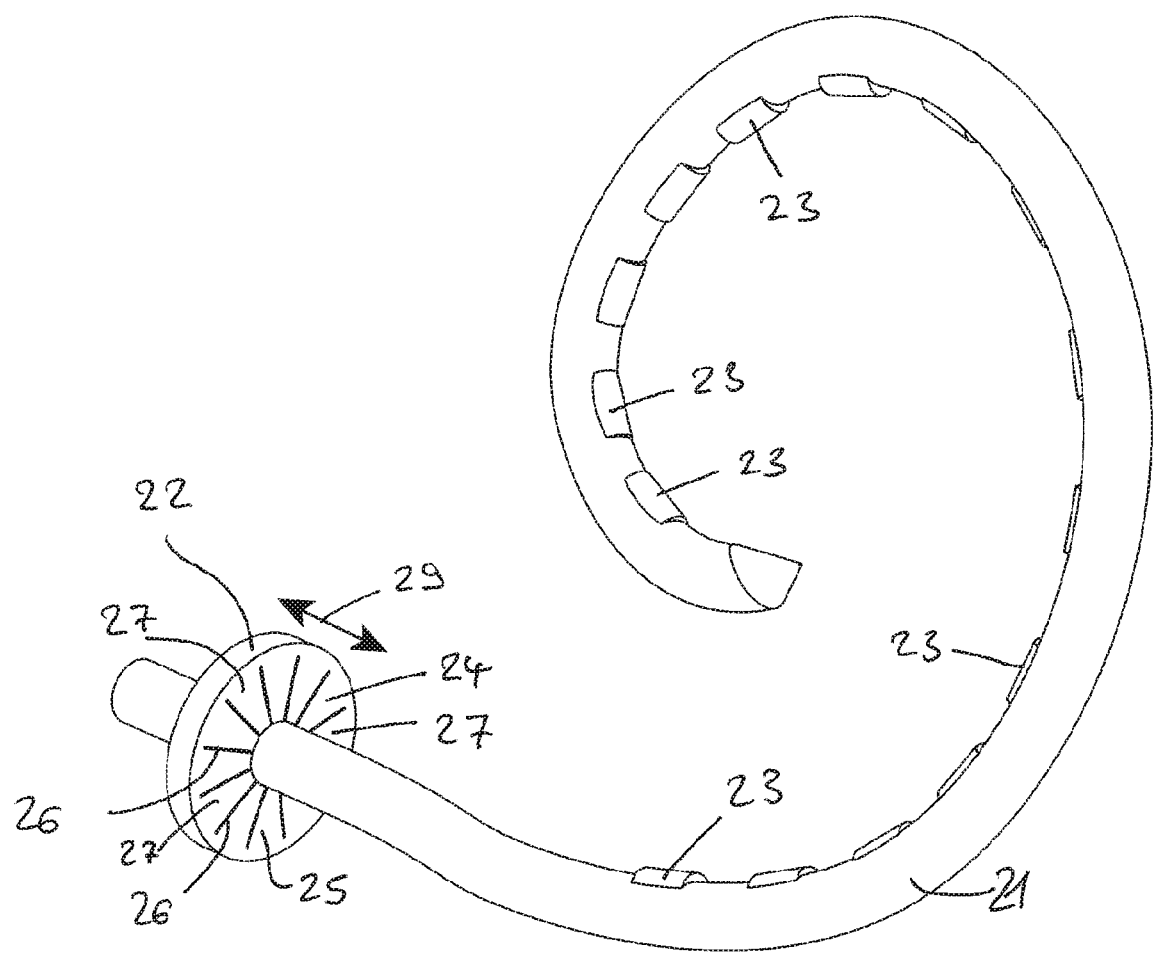

2008/0064918 A1    3/2008  Jolly
2012/0053393 A1*  3/2012  Kaltenbacher ......... H04R 17/00
                                                      600/25
2012/0136197 A1    5/2012  Van Gerwen

OTHER PUBLICATIONS

"International Application No. PCT/EP2016/051713, International Search Report dated Apr. 18, 2016", (Apr. 18, 2016), 2 pgs.
"International Application No. PCT/EP2016/051713, Written Opinion dated Apr. 18, 2016", (Apr. 18, 2016), 6 pgs.

* cited by examiner

ELECTRO-ACOUSTIC IMPLANT

PRIORITY APPLICATIONS

This application is a U.S. National Stage Filing under 35 U.S.C. 371 from International Application No. PCT/EP2016/051713, filed on 27 Jan. 2016, and published as WO2016/124465 on 11 Aug. 2016, which claims the benefit of priority to German Application No. 10 2015 101 482.3, filed on 2 Feb. 2015; which applications and publication are incorporated herein by reference in their entirety.

The invention relates to an electro-acoustic implant having an elongate electrode carrier that has a plurality of stimulation electrodes and having a flat sound transducer that can be excited to vibrate at least section-wise by application of a voltage.

Patients having hearing loss close to deafness can today be successfully fitted with cochlea implants (CIs). Approximately 20% of the patients with a CI indication have a pronounced residual hearing at frequencies <1 kHz that corresponds to a hearing capability with moderate to medium hearing loss. On a regular fitting of a CI, there is a risk for the patient of losing this residual hearing due to the invasiveness of the electrode implantation.

Hearing systems for the supply of patients with a high degree of hearing loss, but with residual hearing are based on an electro-acoustic stimulation of the acoustic organs. It is known to introduce a cochlea implant electrode into the cochlea to excite the auditory sense cells for high frequencies. A conventional hearing aid can be worn in the auditory canal in this respect for the acoustic stimulation of the low frequencies. In this respect, amplified sound waves are emitted by a loudspeaker to the air column in the auditory canal. The amplified vibrations are ultimately transmitted to the cochlea via the eardrum and the auditory ossicle.

It is problematic in the prior art that the implantation is normally very complex and complicated. Most solutions require a hearing aid worn visibly at the outer ear. The sound quality is frequently restricted due to feedback and distortion via the auditory canal and a number of devices only work with an intact middle ear.

It is the object of the present invention to overcome the disadvantages of the prior art.

This object is achieved by the electro-acoustic implant in accordance with claim 1. The dependent claims provide advantageous further developments of the electro-acoustic implant in accordance with claim 1.

In accordance with the invention, an electro-acoustic implant is provided, that is a hearing aid that can inter aria electrically stimulate organs of hearing of a patient to generate an aural impression.

In accordance with the invention, the electro-acoustic implant has an elongate electrode carrier having a plurality of stimulation electrodes. The elongate electrode carrier is designed such that it can be introduced into cochlea of a patient. Auditory sensory cells in the cochlea can be electro-acoustically stimulated by the plurality of stimulation electrodes.

The electro-acoustic implant in accordance with the invention moreover has a flat sound transducer that is excitable to vibrate at least section-wise by applying a voltage. The fact that the sound transducer is of a flat design in this respect means that at least that region of the sound transducer that is excitable to vibrate by applying a voltage extends in a flat manner. Optionally, the flat region can also extend in a plane. An upper side and a lower side of the flat region are preferably in parallel with one another.

In accordance with the invention, the sound transducer is designed such that it can be arranged on and/or in front of a round window or an oval window or a surgically created third window of an ear of a patient and/or can be arranged in a round window niche of an ear such that it at least partially or completely covers the corresponding window. In this respect, the region of the sound transducer of flat design preferably extends over at least some of the surface of the corresponding window. The sound transducer can in this respect optionally be designed such that it can be arranged in the corresponding window such that its region capable of vibrating extends in an opening plane of the corresponding window. The sound transducer therefore preferably at least partially or completely covers the corresponding window.

The sound transducer is arranged in accordance with the invention such that vibrations of the sound transducer effect sound vibrations through the corresponding window. If the sound transducer is arranged in the corresponding window, vibrations of the sound transducer preferably effect sound vibrations that emanate from the corresponding window in the direction of the cochlea.

In accordance with the invention, the elongate electrode carrier extends in the implanted state through the plane/surface of the flat sound transducer that extends in the implanted state at least partially across the corresponding window. The corresponding surface is therefore pierced by the electrode carrier in a part region. In an optional embodiment of the invention, an elongate direction of the electrode carrier can stand perpendicular on the named surface of the sound transducer in that section of the electrode carrier in which it passes through the sound transducer.

The membrane of the corresponding window regenerates after the implantation and then surrounds the electrode carrier. The actuator displaces the fluid in the cochlea over the regenerated membrane.

In an advantageous embodiment of the sound transducer, the flat sound transducer has a membrane structure as part of its named surface. The membrane structure can in particular advantageously be the surface of the sound transducer. The flat region of the sound transducer is therefore the membrane structure in this case. Other parts of the sound transducer such as an optional suspension of the membrane structure can have a non-flat design.

The membrane structure has at least one carrier layer as well as at least one piezo layer, that comprises at least on piezoelectric material, arranged on the carrier layer. In this manner, the sound transducer can be excitable to vibrate at least regionally by applying a voltage to the piezo layer. The piezo layer is preferably arranged directly on the carrier layer. The carrier layer and the piezo layer preferably extend in parallel with one another.

In an advantageous embodiment, the surface of the described membrane structure can be separated by at least one cutting line that separates all the layers of the membrane structure into one, two or more segments such that the membrane structure is mechanically decoupled at the cutting line. A division of the membrane surface in this respect means that the total membrane, that is both the at least one carrier layer and the at least one piezo layer as well as optionally electrode layers, are divided by common cutting lines such that the membrane is mechanically decoupled at the cutting line or lines. Mechanical decoupling in this respect means that two regions of the membrane structure separated by a cutting line are movable independently of one another. The division or segmentation of the membrane surface therefore means a corresponding segmentation of the carrier layer and a corresponding segmentation of the piezo layers and optionally of the electrode layers.

The segmentation enables a high amplitude of a vibration with a very small construction size without the force becoming too low by this measure.

A coupling of a sound transducer as close as possible to the round window (fenestra *cochleae*) or to the oval window (fenestra ovalis or vestibularis) is advantageous for the audiological quality of a hearing aid equipped with the sound transducer, in particular as a sound generator. A sound transducer arranged in front of the round or oval window is moreover implantable by an implanting surgeon via access through the outer auditory canal and eardrum in a relatively short time, possibly even only on an out-patient basis.

The membrane structure is therefore preferably configured such that the sound transducer can be arranged in or before a round window or an oval window or a surgically prepared third window of an ear such that it at least partially or completely covers this window. The sound transducer can in this respect be arranged in the case of a sound generator having the membrane structure such that vibrations of the membrane structure effect sound vibrations through the round or oval window. The membrane structure can in this respect preferably also be in direct contact with the membrane of the corresponding window.

The sound transducer and the membrane structure are particularly preferably configured such that the sound transducer can be introduced in a niche in front of the oval or round window of an ear, i.e. the round window niche, on the basis of the average of the population or the majority of the population. In this respect, an acoustic coupling between the membrane structure and the corresponding window membrane can be established, on the one hand, by introducing material between the membrane structure and the window membrane, contacting both. It is, however, preferred if the membrane structure is arranged at the round or oval window such that it directly contacts the membrane of the corresponding window, but with it being permitted that layers for passivation of or sealing the membrane structure are arranged between the actual membrane structure and the corresponding window membrane.

Sound vibrations are understood in the sense of the application as vibrations that are perceptible to human hearing, i.e. vibrations between approximately 2 Hz and 20,000 to 30,000 Hz. The sound vibrations are moreover suitable to excite sound waves in a medium, in particular air or the perilymph.

Sound vibrations can advantageously be generated by the corresponding window. This can mean that sound waves that emanate from the corresponding round or oval window can be excited by the sound transducer in the inner ear. Sound waves emanating from the corresponding window can therefore advantageously be generated in that the membrane structure in, on or in front of the corresponding window is set into vibration and the perilymph, that is a fluid medium in the inner ear, is directly excited to vibrate or excites a window membrane to vibrate that then in turn excites the perilymph.

The membrane structure can advantageously have at least one carrier layer as well as at least one piezo layer, that comprises at least one piezoelectric material, arranged on the carrier layer. The carrier layer and the piezo layer can form a bimorphic structure and can be arranged and configured such that the membrane structure can be set into vibration by application of a voltage, in particular of an AC voltage, to the piezo layer and/or such that voltages generated by vibration of the membrane are detectable in the piezo layer.

The carrier layer and the piezo layer can for this purpose be arranged on or at one another with parallel layer planes and should preferably be directly or indirectly connected to one another. The named cutting lines preferably separate all the layers of the membrane structure.

To ensure a good audiological quality, the membrane structure is preferably configured such that it enables a maximum deflection of 1 to 5 µm, preferably of 5 µm. A driving force of $2\pi v\, Z_F A^2 x = 1.6\, 10^{-2}$ N is necessary with a frequency of e.g. 4 kHz, an acoustic flow impedance ZF of the round window of 32 GΩ and a surface A of the membrane of the round window of approximately 2 mm$^2$. The average energy corresponds to half the product of the maximum force and the maximum deflection, that is in this example $4 \cdot 10^{-8}$ J, to maintain the power. Converted to a construction space of e.g. 2 mm$^3$, an energy density of 20 J/m$^3$ is accordingly required in this example.

The segments can be designed, in particular with respect to their length, such that the impedance is at its optimum.

The membrane structure is particularly preferably designed in thin film technology for this purpose. Thin films are advantageous since high fields are required to generate high energy densities, whereas, however, due to the biological environment, the voltages that can be applied should be as low as possible. The required energy densities can be achieved particularly advantageously in a thin-film membrane.

In this respect, the piezo layers can in particular advantageously be manufactured in thin film technology. For this purpose, piezo material in the thickness of the piezo layer is applied for a piezo layer of the membrane structure to be produced. The application can take place via deposition technologies such as physical vapor deposition sputtering, chemical vapor deposition sputtering, sol-gels and others. Much thinner piezo layers can be prepared by the production of the piezo layers through deposition of piezo material in the desired thickness than in accordance with the prior art where fully grown piezo crystals were ground down to the thickness of the piezo layer.

The piezo layers preferably have a thickness of ≤20 µm, preferably ≤10 µm, particularly preferably ≤5 µm and/or ≥0.2 µm, preferably ≥1 µm, preferably ≥1.5 µm, particularly preferably=2 µm. The electrode layers preferably have a thickness of 0.5 µm, preferably ≥0.2 µm, particularly preferably ≥0.1 µm and/or ≥0.02 µm, preferably ≥0.05 µm and particularly preferably ≥0.08 µm Thin films of the sound transducer—both those of the silicon beam structure and those of the piezo layer(s)—ensure that only a small mass is set into motion on a deflection of the beams. The resonant frequency of the vibration system for the described actuator variants is located in the upper range of the frequency bandwidth of human hearing.

The generation of the mechanical vibrations of the sound transducer is based in this respect on the principle of elastic deformation of a bending beam, with the membrane or segments of the membrane being able to be considered as bending beams. The piezoelectric layer (piezo layer) can in this respect be shortened and/or lengthened by application of the voltage and of the electric field that can hereby be generated. Mechanical strains are in this respect generated in the material composite of carrier layer and piezo layer that result in an upward bending of the beam or of the membrane structure with a shortening piezo layer and in a corresponding downward movement with a lengthening piezo layer. Whether the piezo layer lengthens or shortens depends in this respect on the direction of polarization of the piezo layer and on the direction of the applied voltage or of the applied electric field.

With a single-layer sound transducer, the described carrier layer can carry a single layer of piezoelectric material. In addition to this, electrodes can form further components of the layer setup. A bottom electrode can in this respect be applied directly or via a barrier layer to a silicon substrate, whereas a top electrode can be located on the piezoelectric layer. The direction of polarity of the piezoelectric material is preferably perpendicular to the surface of the silicon structure. If an electric voltage is applied between the top electrode and the bottom electrode and if an electric field is formed, the piezo material shortens or lengthens (in dependence on the sign of the voltage) in the longitudinal direction of the beam due to the transverse piezoelectric effect, mechanical strains are generated in the layer composite and the beam structure undergoes bending.

It is preferred for the membrane structure to have a circular or oval periphery. It is in particular favorable in this respect if the periphery of the membrane structure corresponds to the periphery of the round or oval window of an ear so that the peripheral line of the membrane structure runs in parallel with the periphery of the round or oval window when the sound transducer is implanted.

The sound transducer can be placed directly onto the membrane of the round window through a round or slightly oval shape. Since the round window membrane can be considered fixedly clamped in at its bony border and does not show any vibration deflection there, the maximum vibration deflections occur at the geometrical center of the membrane. If the sound transducer is now positioned centrally on the round window membrane, the maximum deflections of the transducer and the membrane are superposed so that a good audiological coupling and a large sound amplification potential is achieved by the transducer. An n-cornered periphery of the membrane structure where n is preferably ≥8 is also possible.

It is further in particular preferred in the case of a circular periphery, but also with other shapes of the membrane structure, for the cutting lines that divide the membrane surface into segment to extend radially from a margin of the membrane structure in the direction of a center of the membrane. In this respect, the cutting lines do not have to start directly at the margin and do not have to reach up to the center, it is also sufficient for the cutting lines to extend from the vicinity of the margin up to and into the vicinity of the center. If, however, the cutting lines do not reach the center, there should be a free region at the center in which the cutting lines end such that the mechanical decoupling of the segments is ensured at that end facing the center.

The segments can be configured in this respect such that they are in the shape of slices of a cake, that is have two margins extending at an angle to one another as side margins as well as one outer margin that extends at the periphery of the membrane structure in parallel with this periphery. At the other end of the side margins, opposite the outer margin, the segments can taper to a point or can be cut off such that a free region results around the center. In an advantageous embodiment, the electrode carrier can extend through this free region.

The segments can be fixedly arranged at the outer margin at the margin of the membrane structure and can be independent of one another at the side margins and optionally at that margin facing the center such that they can oscillate freely around the outer margin. The greatest deflection will in this respect normally occur at that end of the segment facing the center. The number of the segments is preferably ≥8.

The cutting lines can in this respect extend in a radially straight manner so that the segments have straight radial edges.

It is, however, also possible that the radially extending cutting lines extend in curved form so that segments result having edges that to not extend in a straight radial manner. Segments can in particular hereby be formed that extend in an arcuate or wave-shaped manner or along a zig-zag line in the radial direction. A number of other geometries are conceivable.

In an alternative embodiment of the invention, the membrane structure can be spirally structured by at least one cutting line. The at least one cutting line in this respect extends such that at least one spiral segment results that preferably twists about a center of the membrane structure. It is also possible to provide a plurality of cutting lines that divide the membrane structure such that two or more spiral segments result that advantageously each wind about the center of the membrane structure and particularly preferably run into one another. The spiral structure can have an opening at its center through which the electrode carrier can extend.

To set the membrane structure into vibration and/or to tap a voltage at the piezo layer, at least one first electrode layer and at least one second electrode layer can be arranged at the membrane structure, with the at least one piezo layer being arranged between the first and second electrode layers. The electrode layers in this respect preferably cover the piezo layer and are arranged with parallel layer planes at or on the piezo layer. The first or second electrode layers are preferably arranged between the carrier layer and the piezo layer such that the piezo layer is arranged above one of the electrode layers on the carrier layer. The piezo layer and the electrode layers particularly preferably completely cover one another.

The use of segment structures allows a higher deflection with respect to an unstructured membrane since the beam elements can deform freely where they are separated by the cutting lines, e.g. at the center of the disk, and thus undergo constant bending in only one direction. The deformation of a contiguous membrane is in contrast characterized by a change of direction of the curvature, which produces smaller deflections.

In a preferred embodiment, the membrane structure has a plurality of piezo layers arranged on one another with parallel surfaces, with an electrode layer being arranged between two respective adjacent piezo layers. A respective electrode layer and a piezo layer are therefore arranged alternately on the carrier layer. Electrode layers and piezo layers can be arranged directly on one another, connected to one another or arranged on one another via one or more intermediate layers. With this embodiment, vibrations having a particularly large force or power can be produced and vibrations can be detected particularly exactly.

With this transducer modification, electrodes having a different electric potential therefore alternate with piezo layers in the layer design. The silicon structure is first followed by a bottom electrode, then by a first piezo layer, by an electrode having an opposite potential, by a second piezo layer, by an electrode having the potential of the bottom electrode, etc.

The direction of polarization of the individual piezo layers can, as in the single-layer transducer, be disposed perpendicular to the surface of the membrane structure; however, it faces in the opposite direction for alternating piezo layers. The electrical field being built up between the electrodes of opposite potential and the direction of polarization alternating for the individual piezo layers provides a common length change of the total layer design, which in turn causes a bending of the silicon structure.

The electrode layers are advantageously configured or contacted such that two respective adjacent electrode layers can be acted on by a charge of different polarity. An electric field can hereby be generated in the piezo layers that respectively extends from one electrode layer to the adjacent electrode layer. In this manner, the piezo layers can be particularly uniformly interspersed with electric fields. In the case of a vibration detection, different signs of a voltage arising at the piezo layer can preferably respectively be tapped by adjacent electrode layers.

In a further advantageous embodiment of the present invention, at least two ribbon-shape, that is elongate, electrodes that form an electrode pair can be arranged on the surface of the at least one piezo layer or on the surface of the carrier layer such that they extend in parallel with the corresponding surface and preferably also extend in parallel with one another. The two electrodes of an electrode pair can each be acted on by a charge of a different polarity such that an electric field that at least regionally passes through the piezo layer is formed between the electrodes of an electrode pair. If a plurality of electrode pairs are provided, an electric field that passes through the piezo layer can also be formed between electrodes of different polarity of adjacent electrode pairs. In the case of a vibration detection, different signs of the bottom voltage can accordingly be contacted by a respective electrode of the electrode pair.

The conductor trace structures of the ribbon-shaped electrodes can preferably have a rectangular cross-section.

It is particularly advantageous for a plurality of electrode pairs each having two electrodes that can be acted on with different polarity to be arranged such that the electrodes of the plurality of electrode pairs extend in parallel with one another. In this respect, the electrode pairs should moreover be arranged such that a respective two electrodes extending adjacently can be acted on by a charge of different polarity. In this manner, an electric field passing through the piezo layer is formed between two respective adjacent electrodes. For the event that, as described here, a plurality of electrode pairs are provided, there are therefore a plurality of electrodes on a surface of the piezo layer or of the carrier layer that can extend in parallel with one another and that can be arranged next to one another with alternating polarity.

The polarity of the piezo material is in this case preferably not distributed homogeneously over the total piezo layer; the direction of polarization rather preferably extends in the form of field lines from the negative electrode to the positive electrode. If the comb-shaped electrodes are acted on by changing electric potential in the operation of the transducer, an electric field is formed along the direction of polarization of the piezo material and the piezo material extends or shortens along said electric field. The total piezo layer thereby lengthens or shortens in the longitudinal direction of the beam, which results in a downward bending or upward bending of the silicon structure.

It is particularly advantageous for the electrodes in this respect additionally to extend in parallel with the margin of the membrane structure. If the membrane structure is therefore circular, the electrodes can preferably form concentric circles around the center of the membrane structure. The electrodes are also preferably accordingly configured as oval with an oval membrane structure. The electrodes can each extend along the total periphery in parallel with the periphery of the membrane structure or only over a part of the periphery so that they each have the shape of sections of the circumference of a circle, for example.

Ribbon-shaped electrodes can particularly advantageously be contacted over common conductors, with a plurality of the electrodes being contacted by a common conductor. A plurality of the electrodes of one polarity can thus be connected to at least one first conductor and electrodes of the other polarity can be connected to at least one second conductor. So that the electrodes of different polarity are arranged alternately, the electrodes of different polarity associated with the different conductors can engage into one another like combs. The common conductors can in this respect intersect the electrodes of the polarity corresponding to them and particularly preferably extend radially e.g. with circular electrodes.

The membrane structure can also be of a multi-layer configuration in the case of a ribbon-shaped design of the electrodes. It is in turn possible in this respect, on the one hand, that a plurality of piezo layers are arranged on one another, with then ribbon-shaped electrodes being able to extend between two respective adjacent piezo layers. The arrangement of the electrodes in this respect corresponds to the above-described arrangement on the surface of a piezo layer. It is, however, also possible that the membrane structure has at least one piezo layer that is interspersed by ribbon-shaped electrodes or electrode pairs in one or more planes. In this case, the electrodes of the electrode pairs extend in the interior of the corresponding piezo layer. The different possibilities of the arrangement here also correspond to those of the above-named arrangement on the surface of the piezo layer.

This variant of the sound transducer has a thicker piezo layer with respect to the previous solution that can be traversed by a plurality of layers of comb-shaped electrodes. The polarization in the piezo material in turn extends in the form of field lines from the negative to the positive conductor trace electrodes. When a voltage is applied, an electric field is formed along the direction of polarization and results in an extension or shortening of the piezo material along the field lines and in a downward bending or upward bending of the beam structure.

In the case of spiral segments, ribbon-shaped electrodes can be arranged along the longitudinal direction of the segments. One electrode pair is preferably sufficient here.

Since the sound transducer is used in a biological environment, it is advantageous for the voltage at which the electrodes are acted on to be smaller than 3 volts, preferably smaller than 2 volts, particularly preferably smaller than 1.3 volts. Alternatively or additionally, it is also possible to encapsulate the electrodes in a liquid-tight and/or electrically insulating manner such that they do not come into contact with a fluid optionally surrounding the sound transducer. Such a tight encapsulation will, however, have such a high acoustic impedance that considerably audiological losses are to be anticipated.

Since the piezoelectric effect is proportional to the strength of the electric field that passes through the material in the observed region, such high fields can be generated by use of very thin piezoelectric layers with a very small distance of the electrodes (the electric field is calculated in the homogeneous case as the quotient of the applied voltage and the distance of the electrodes) that the piezo effect is sufficient to achieve the vibration deflections and the forces required for the excitation of the round window.

The carrier layer can comprise or consist of silicon.

$PbZr_xTi_{1-x}O_3$ can be considered as the piezo materials with preferably 0.45<x<0.59, particularly preferably with doping amounts of, for example, La, Mg, Nb, Ta, Sr and the like, preferably with concentrations between 0.1 and 10%. Further solid solutions with $PbTiO_3$ such as $Pb(Mg_{1/3}, Nb_{2/3})O_3$, $Pb(Sn_{1/3}Nb_{2/3})O_3$ can be considered. Possible materials also include lead-free materials that contain $KNbO_3$, $NaNbO_3$, doping amounts with Li, Ta, etc., piezo layers containing Bi, aurivillius phases with Ti, Ta, Nb, furthermore also perovskite phases such as $BiFe_3$. Classical thin film materials such as AlN and ZnO are also possible.

Silicon as the carrier material for the piezo layers enables the manufacture of the disk-shaped structure and of the bending beams of the shape of a slice of cake using the structuring techniques of the microsystem technology. Known and tried and tested coating and etching methods of manufacturing beams, electrodes and a piezo layer can be used, e.g. sol-gel techniques, sputter processes, chemical etching, ion etching, etc. Furthermore, the processes of microsystem technology permit a parallelization of the production process; a plurality of sound transducers can be manufactured from one silicon wafer in one production passage. This enables a cost-favorable production.

The at least one piezo layer preferably has a thickness of ≤20 μm, preferably ≤10 μm, particularly preferably ≤5 μm and/or ≥0.2 μm, preferably ≥1 μm, preferably ≥1.5 μm, particularly preferably =2 μm. The electrode layers preferably each have a thickness of ≤0.5 μm, preferably ≤0.2 μm, particularly preferably ≤0.1 μm and/or ≥0.02 m, preferably ≥0.05 μm and particularly preferably ≥0.08 μm. A diameter of the membrane structure is preferably ≤4 mm, preferably ≤3 mm, particularly preferably ≤2 mm and/or ≥0.2 mm, preferably ≥0.5 mm, preferably ≥1 mm, particularly preferably=1.5 mm, and is particularly preferably selected such that the sound transducer can be arranged in a suitable manner in front of the round or oval window of an ear. The sound transducer can preferably be arranged in the round window niche of an ear, with its dimensions being able to be understood as those of the majority or average of the population within the scope of the present document.

The sound transducer in accordance with the invention can be directly coupled by a directly placing of the membrane surface onto a membrane of the round or oval window. Since the maximum vibration deflection of the transducer is superimposed at the geometrical center of the disk with the maximum vibration of the membrane at the center of the round window, a good audiological coupling with high sound amplification potential is possible.

In accordance with the invention, the sound transducer can also have a plurality of membrane structures as described above. These membrane structures are in this respect of the same structure and are arranged in parallel with one another above one another such that the same segments of the structure or the cutting lines of the membrane structures are disposed above one another. The same segments are then coupled to one another such that a deflection and/or a force exertion of one of the segments is transferred to the adjacent segments. The membrane structures can in this respect be arranged above one another such that on the application of a voltage of a given polarization to the sound transducer, all the segments are deflected in the same direction. The membrane structures are of the same orientation in this respect. In this case, a total force can be realized that is higher than that of a single membrane structure. It is also possible to arrange the membrane structures on one another such that adjacent membrane structures are each oriented conversely so that on an application of a voltage of a given polarization, adjacent membrane structures are respectively deflected in different directions. In this case, a total deflection can be realized that is larger than that of a single membrane structure.

The embodiments of the invention can specifically be adapted to the demands of an implantable hearing aid having an audiological excitation of the round or oval window in the middle ear. The sound transducer is preferably a sound generator. It is also possible to fit classical hearing aids that are seated directly on the ear drum or other miniature loudspeakers such as ear phones with the sound transducers in accordance with the invention The sound transducer can moreover be used as a sensor and enables an electric signal to be generated from a sound signal. The sound transducer can therefore also be used as a microphone.

In an advantageous embodiment of the invention, the sound transducer can be fixable in the middle ear of a person such that vibrations of the sound transducer can be transferred to a fluid in the cochlea. There is preferably no air volume between the sound transducer and the fluid so that a good coupling of the sound transducer to the fluid in the cochlea becomes possible.

In an advantageous embodiment of the invention, the elongate electrode carrier can extend through a center of the surface of the flat sound transducer. If the vibrating surface of the sound transducer is segmented as described above, a segmentation can be provided for this purpose that has an opening at the center of the sound transducer in which opening no membrane structure is present.

Some of these embodiments were described above relating to the sound transducer. If the sound transducer and/or its membrane has a circular periphery, this opening can be present at the center of the circle. A segmentation with radial cutting lines such as the above-described segmentation in the form of cake slices is particularly advantageous in this case.

Alternatively, the elongate electrode carrier can extend eccentrically through the surface of the flat sound transducer. In this case, the electrode carrier therefore passes through the surface of the sound transducer away from the center of this surface, but the surface of the sound transducer advantageously completely surrounds the electrode carrier. The surface preferably has a corresponding eccentric opening for such a passage of the electrode carrier through the surface of the sound transducer. The surface of the sound transducer can advantageously also be separated by radial cutting lines for this embodiment. In this case, however, membrane sections arise that are of different lengths. Those membrane pieces in whose direction the electrode carrier is displaced with respect to the center of the surface are shorter in the radial direction, whereas oppositely disposed segments are longer in the radial direction. The segments can in particular be shorter and longer than the corresponding segments in the above-described central passage of the electrode carrier through the membrane.

In a particularly advantageous embodiment of the invention, the elongate electrode carrier can pass through the surface of the flat sound transducer in a notch at the margin of the surface of the flat sound transducer. A notch of the surface of the sound transducer is in this respect a region that is not covered by the surface and that extends from the margin of the surface concavely into the surface of the sound transducer. In an advantageous embodiment of the invention, the electrode carrier can at least contact a margin of the notch on at least a part of its circumference. A radial depth of the notch is preferably equal to a diameter of the elongate electrode carrier. In this manner, the electrode carrier can be led through the sound transducer with a minimal loss of surface capable of vibration.

The elongate electrode carrier is preferably an elongate structure at which a plurality or a large number of electrodes are arranged next to one another in a longitudinal direction of the electrode carrier. The electrodes are in this respect preferably arranged such that they can excite sensory cells in the ear of the person wearing the implant responsible for specific frequencies in the implanted state. The exact position is in this respect preferably individually adapted to the anatomical circumstances of the corresponding person.

The elongate electrode carrier is preferably a cochlea implant electrode whose length is configured such that only frequencies higher than a specific threshold frequency can be excited by it. For this purpose, the electrode carrier can be shortened such that it does not extend into the cochlea down to the total depth, but only down to a specific position that corresponds to the cut-off frequency. The sensory cells are arranged in the cochlea such that sensory cells present deeper in the cochlea detect deeper frequencies than further outwardly disposed sensory cells. The frequency excited by the electrodes can therefore be limited toward the bottom by a limitation of the length of the electrode carrier. The length of the electrode carrier is preferably designed such that only frequencies 1000 Hz, preferably ≥1300 Hz, particularly preferably ≥1500, can be excited by the cochlea implant electrodes of this electrode carrier in the implanted state.

In an advantageous embodiment of the invention, the sound transducer can be displaceable with respect to the electrode carrier in a longitudinal direction of the electrode carrier. The electrode carrier can hereby initially be introduced down to the intended depth in the cochlea on the implanting of the electro-acoustic implant. The actuator on the electrode can then advantageously subsequently be pushed forward up to the corresponding window and the front actuator surface can be brought into direct contact with the cochlea. If both the components, that is the sound transducer and the electrode carrier, are accommodated at the intended location, they can be fixed using a fastening element such as a clip or a clamp or alternatively using conjunctive tissue.

In an advantageous embodiment of the invention, the sound transducer can be tiltable with respect to the electrode carrier. The front actuator surface can in this respect therefor advantageously be tilted about one or two axes perpendicular to the longitudinal axis of the electrode carrier. It can hereby be ensured that the actuator lies in a planar manner on the surface of the corresponding window membrane without the electrode carrier having to penetrate into the cochlea at a right angle or at a fixed angle. Such a tilt capability can advantageously be achieved in that a ball joint is provided between the actuator and the electrode carrier. The ball joint can, for example, be configured as a spherical thickened portion of the electrode carrier. Alternatively, a tilt can also be achieved in that the electrode carrier is implemented with a clearance in the radial direction with respect to the longitudinal axis of the electrode carrier and the resulting intermediate space between the sound transducer and the electrode carrier is filled with a flexible material such as silicone. In this case, the opening in the surface of the sound transducer is therefore advantageously larger than the diameter of the electrode carrier. The electrode carrier is therefore at least regionally spaced apart from a wall of the opening. The named flexible material can be provided in this spaced-apart region.

The electro-acoustic implant in accordance with the invention has improved acoustic properties with respect to an acoustic excitation using a conventional hearing aid such as known from the prior art. The sound converter can advantageously be designed such that it has a high resonant frequency and thereby only ensures a flat transmission behavior for the relevant low frequencies at high vibration deflections. A distortion free auditory impression up to high amplifications that can correspond to an outer auditory impression of 120 dB SPL can hereby be achieved and by an advantageous implanting of the implant in direct contact with the cochlea. The risk of feedback can be considerably reduced by an advantageous spatial separation of the microphone (for example at the outside at the head, via the auricle) and the sound transducer (advantageously implanted into the middle ear). A superior sound quality for the relevant low frequencies and thereby an improved speech comprehension for the patients results overall with respect to the prior art.

The described hybrid system is moreover characterized by a hardly elevated operation effort with respect to the implanting of just a cochlea implant, in particular when the electrode and the actuator are positioned at the same point of the cochlea.

A further advantage of the concept is the miniaturization and reduction of the externally non-visible components. The auditory canal can remain free by omitting the conventional hearing aid. The remaining external components such as the microphone, rechargeable battery, and the sound processor can be accommodated in a miniaturized form in a single housing and can be worn almost invisibly in the hair.

The invention will be explained by way of example in the following with reference to some Figures. The same reference numerals in this respect correspond to the same features or to corresponding features. The features described and shown in the examples can also be implemented independently of the corresponding example and can be combined with one another between different examples.

There is shown

Figure 2:
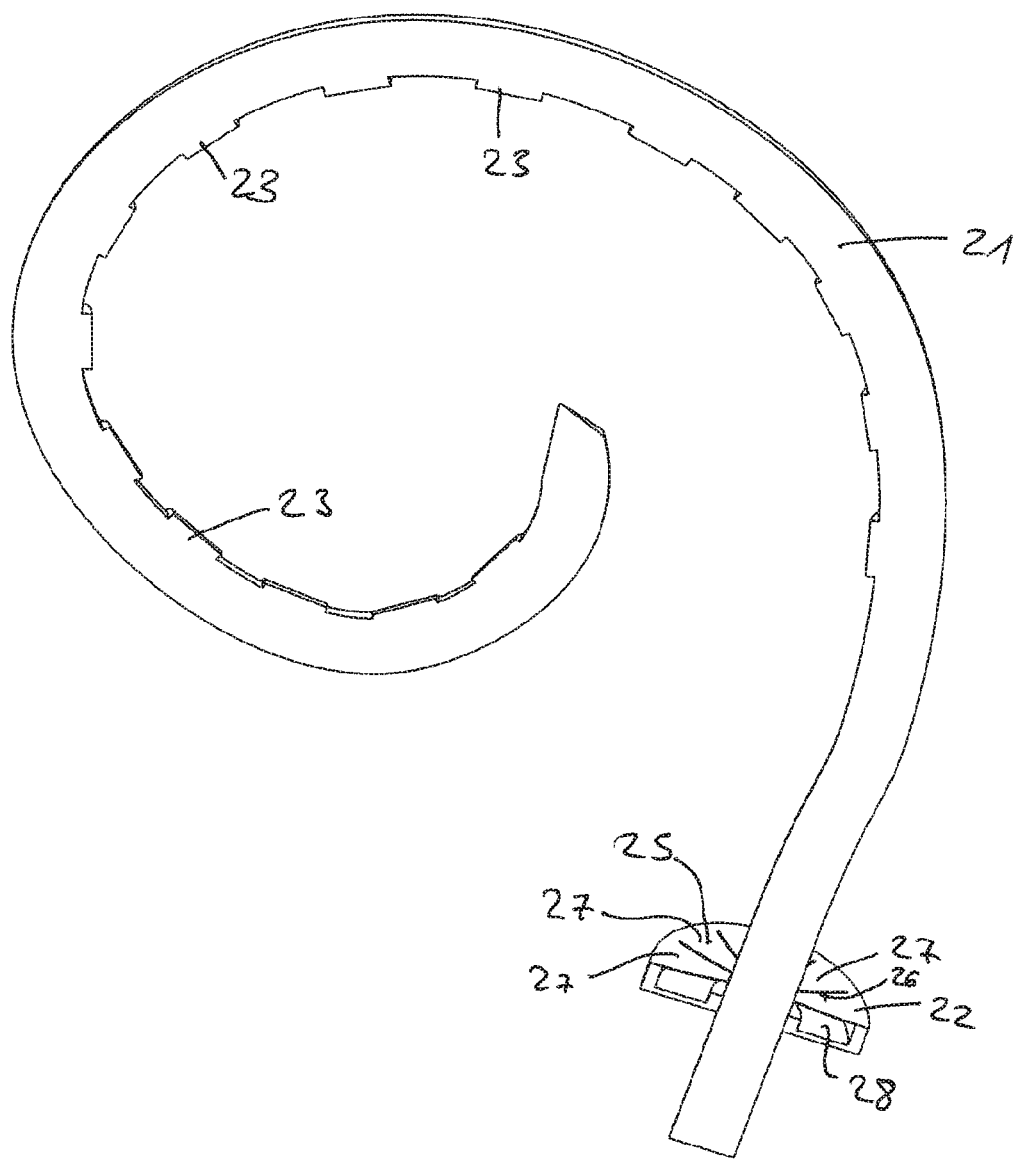
Figure 3:
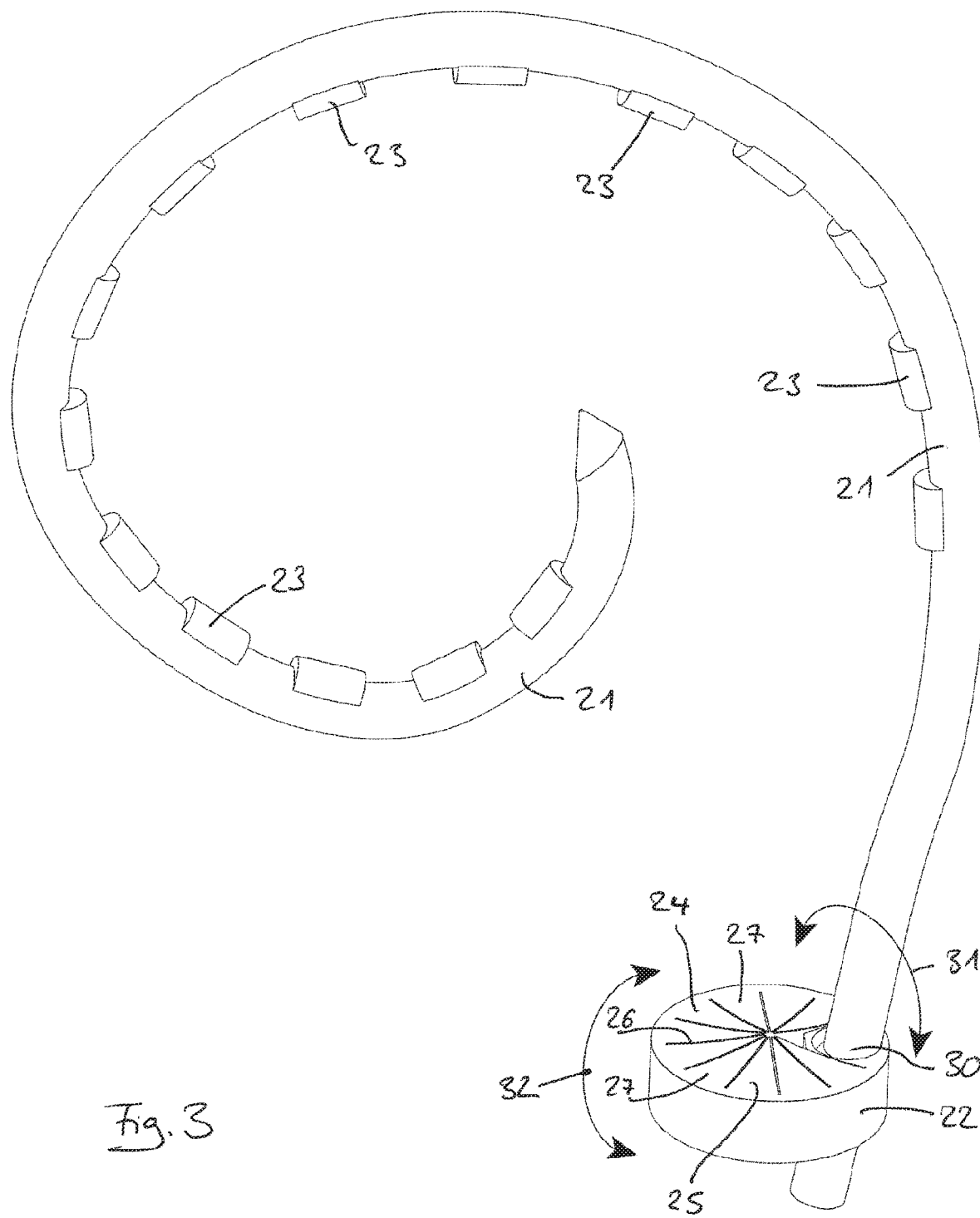
Figure 4:
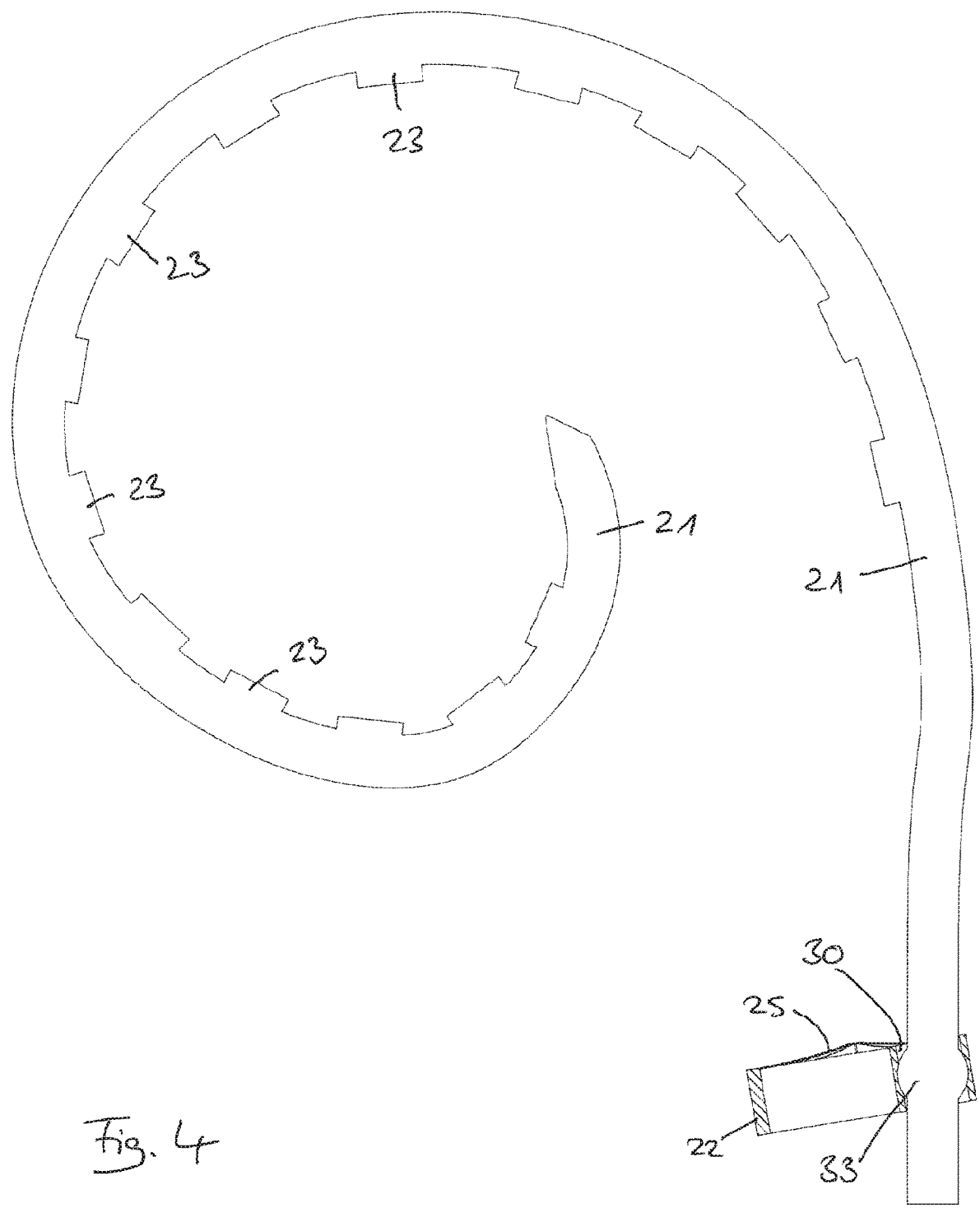
Figure 5:
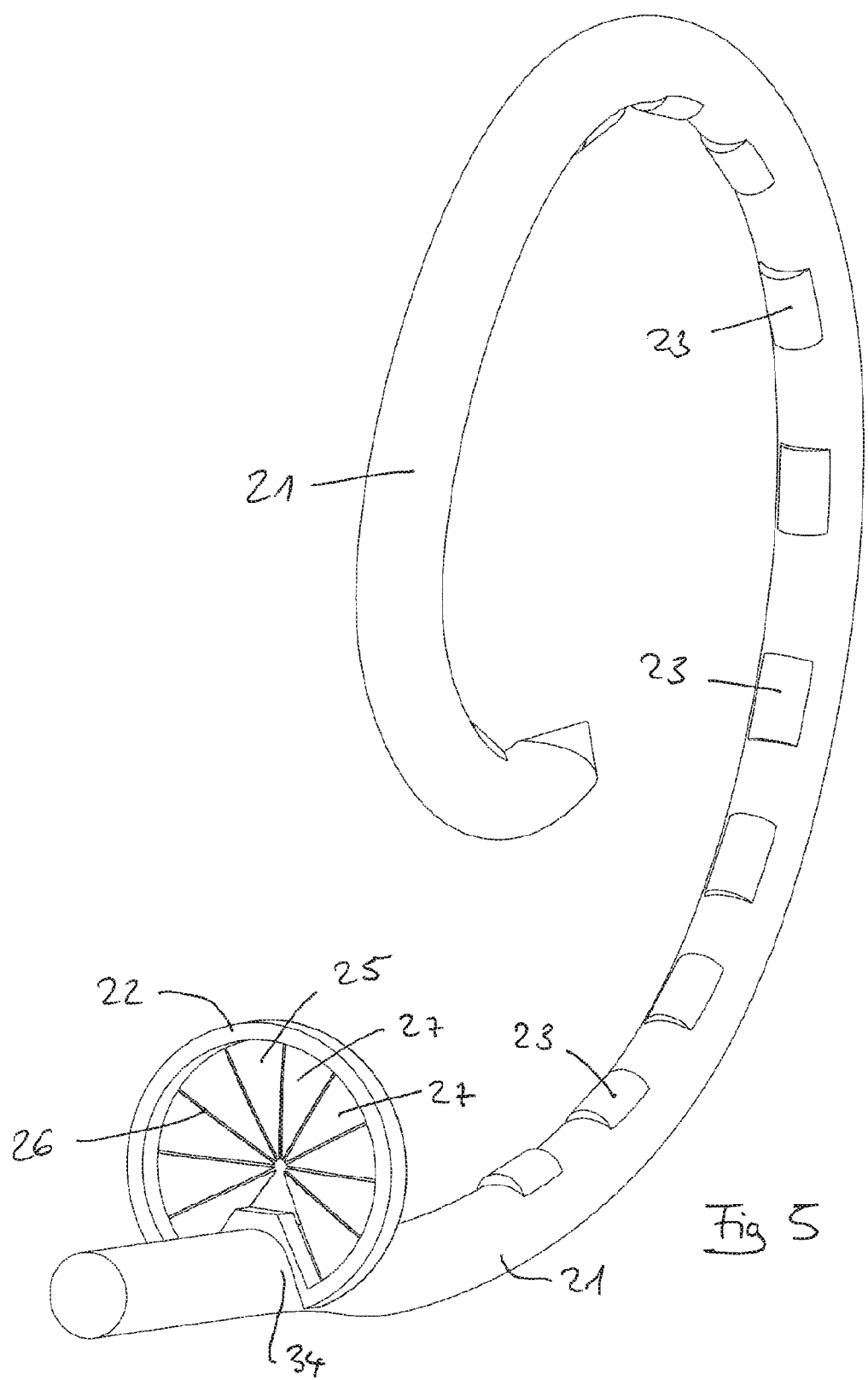
Figure 6:
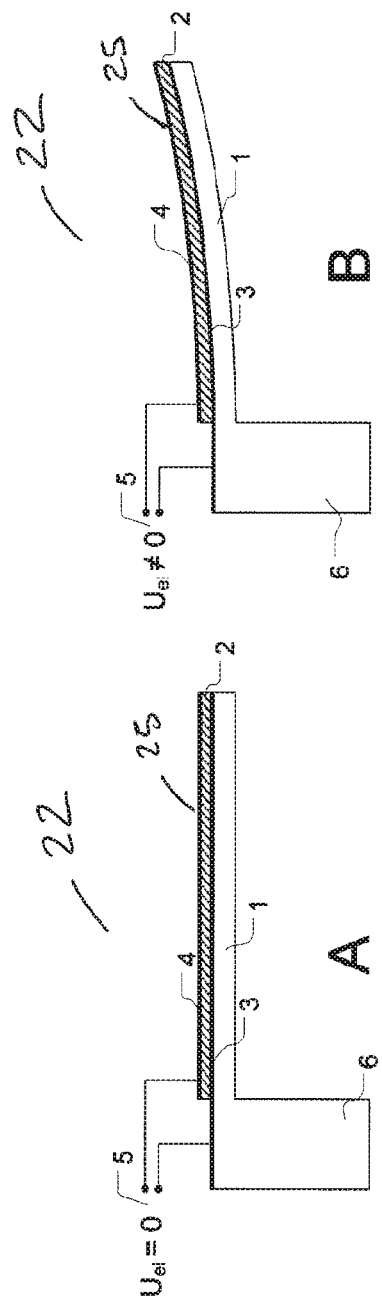
Figure 7:
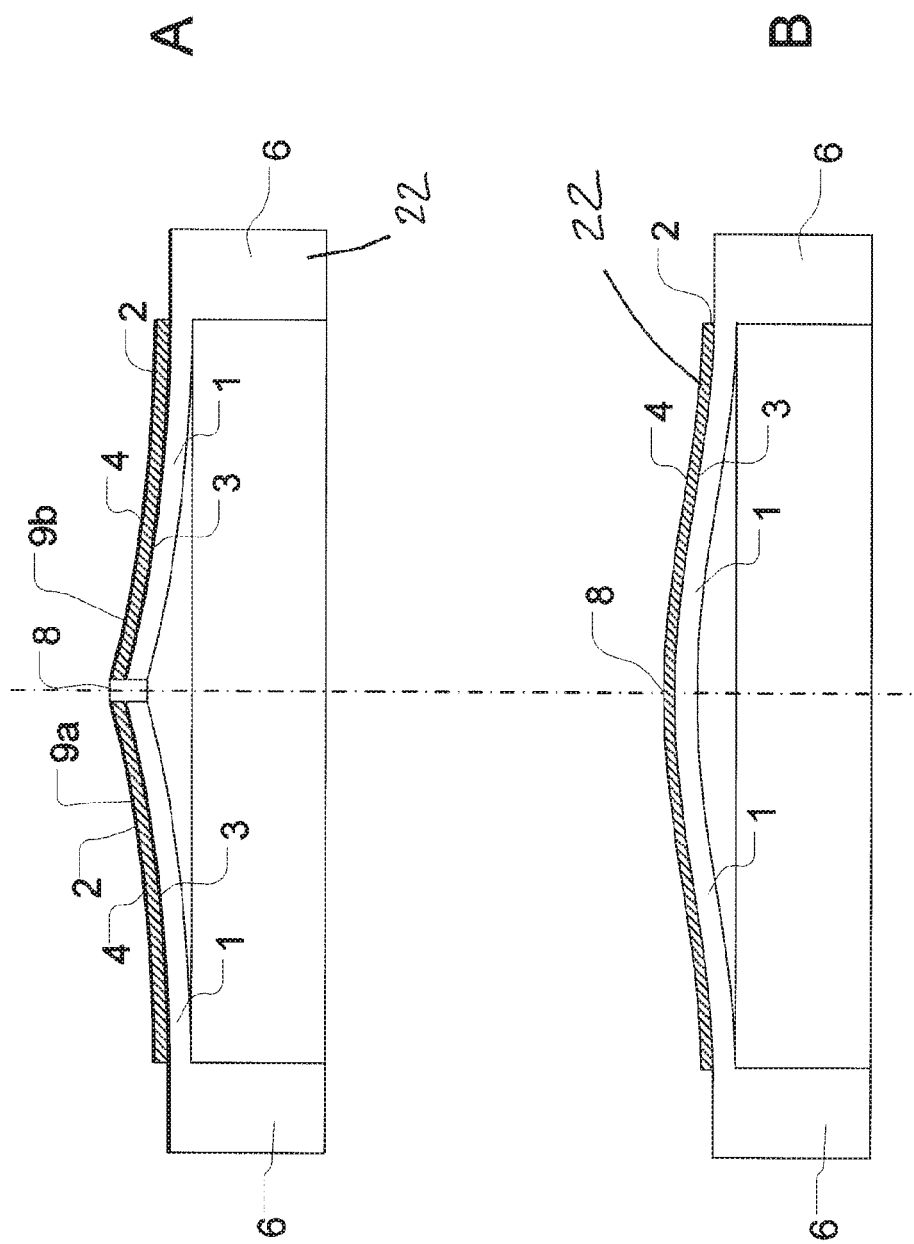
Figure 8:
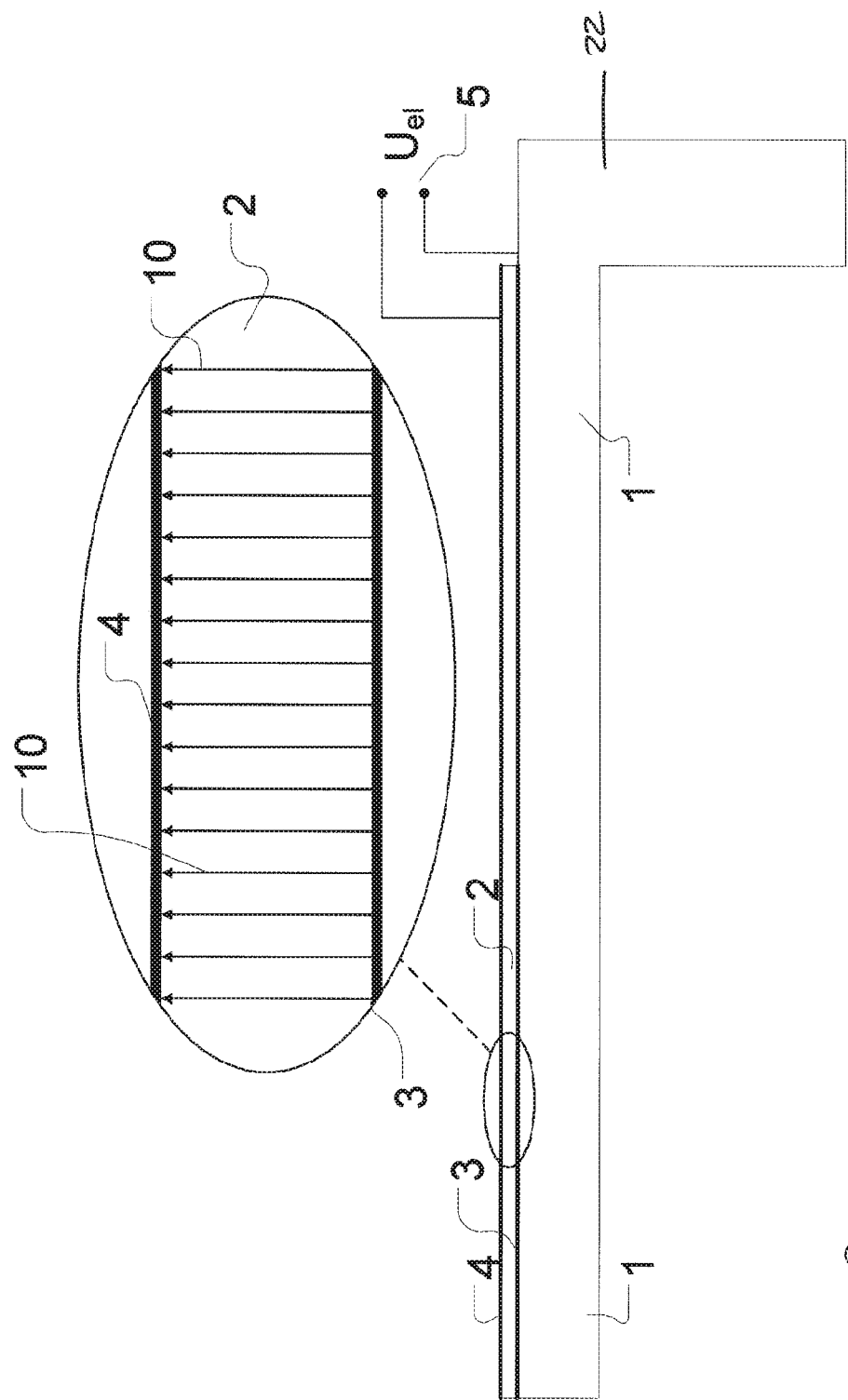
Figure 9:
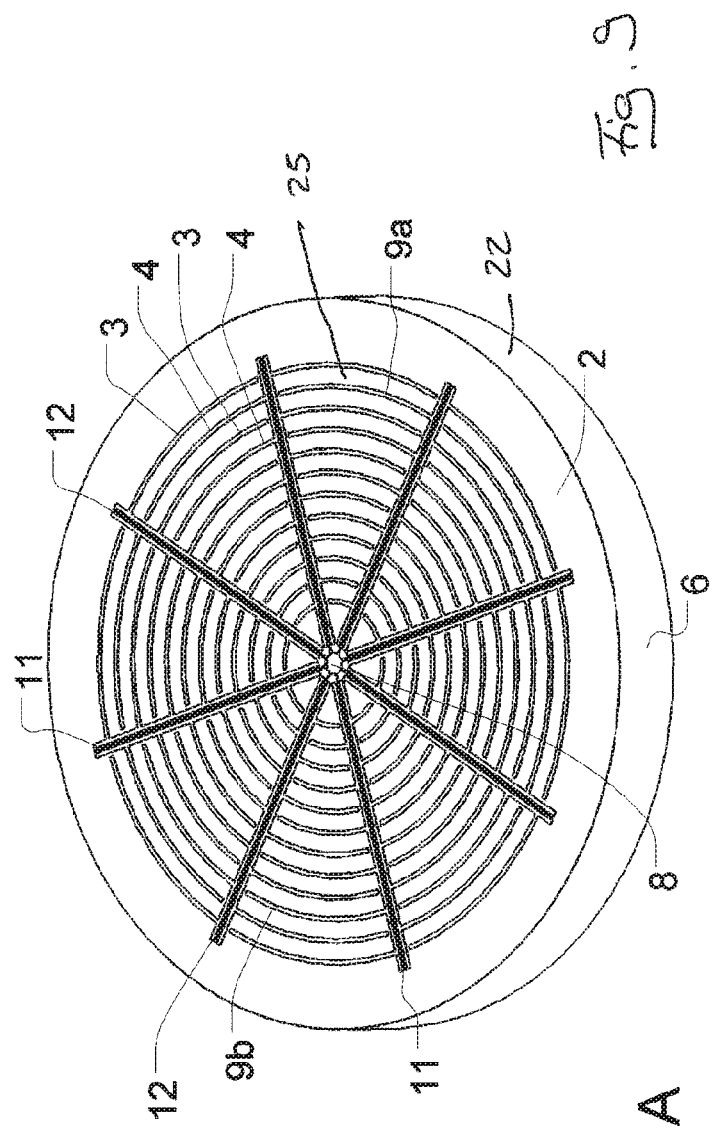
Figure 10:
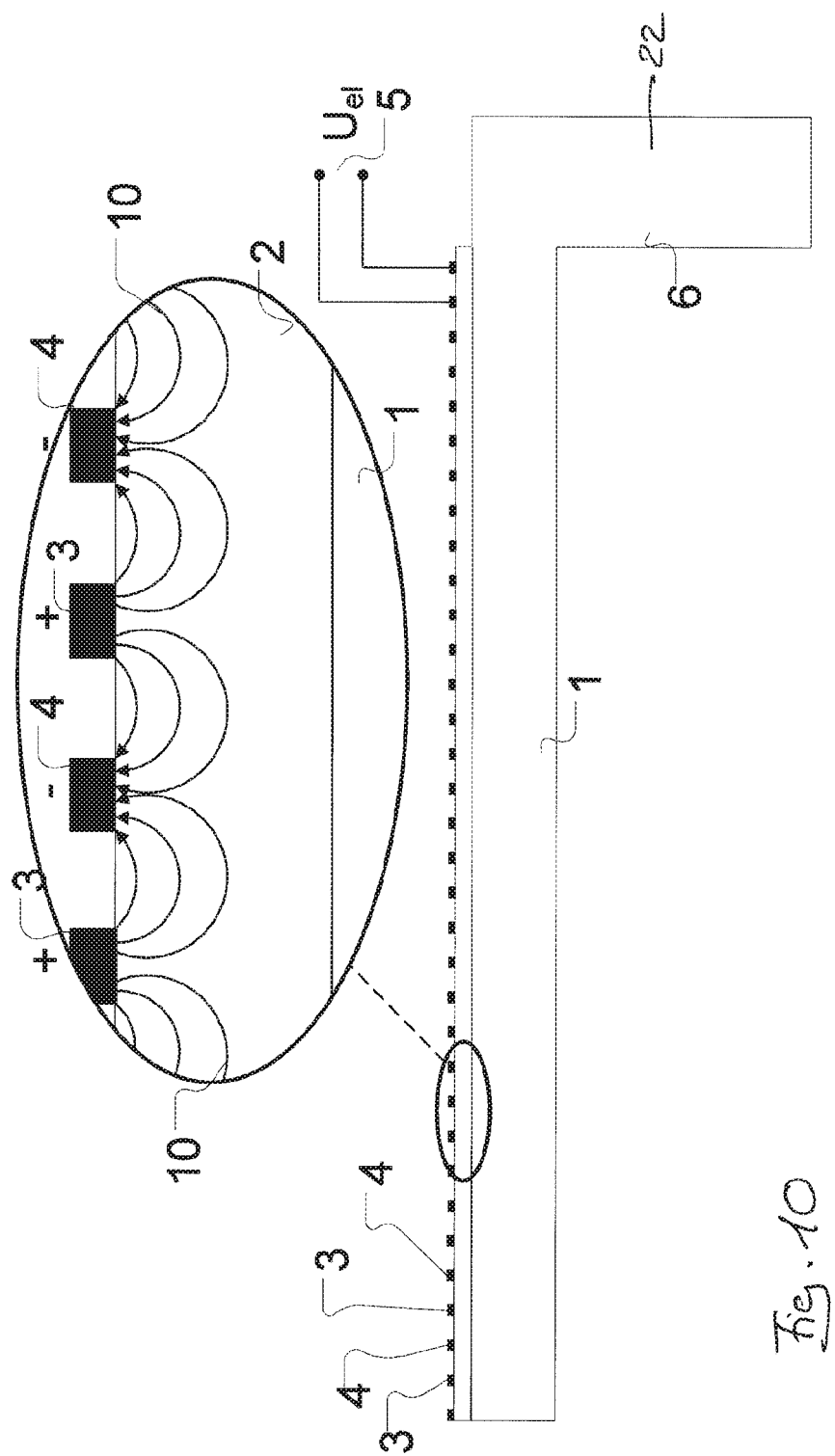
Figure 11:
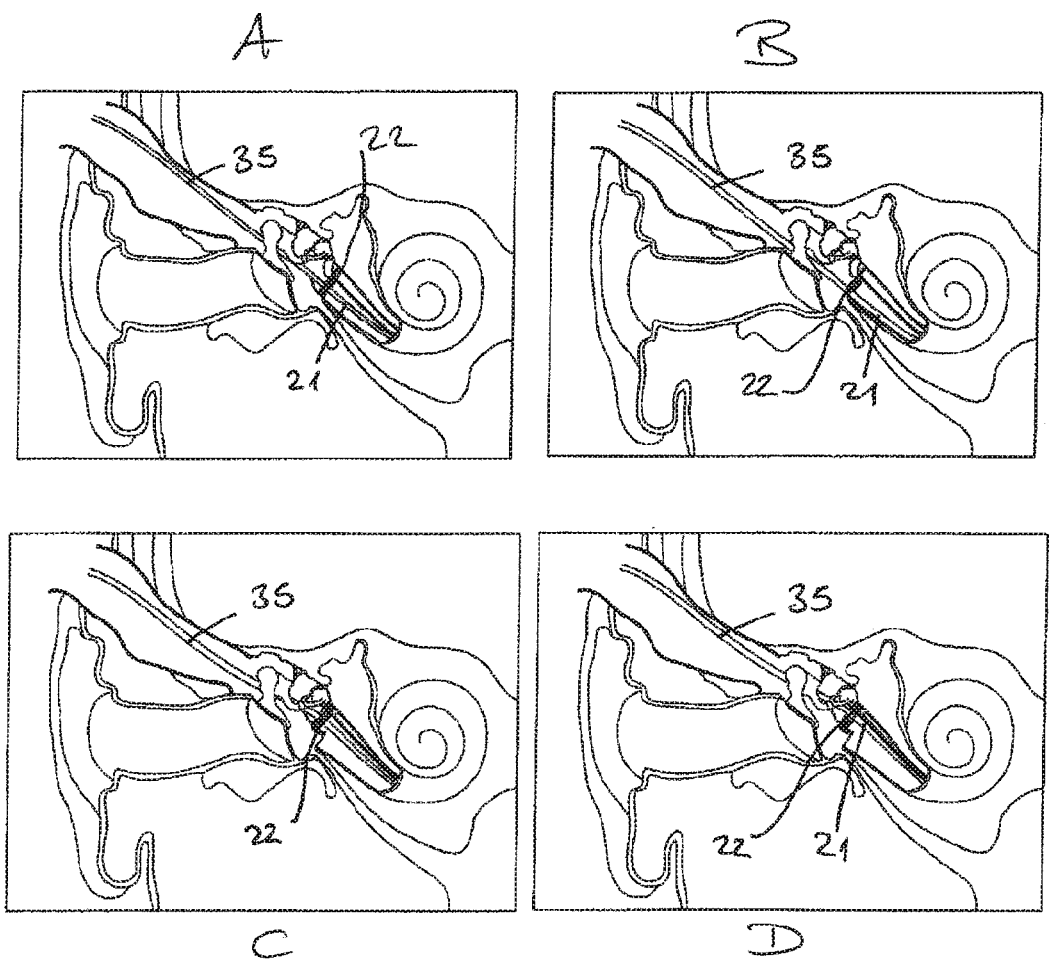

FIG. 1 an electro-acoustic implant in accordance with the invention with an electrode carrier led centrally through a sound transducer;

FIG. 2 a section through the implant shown in FIG. 1;

FIG. 3 an electro-acoustic implant in accordance with the invention with an electrode carrier led eccentrically through the sound transducer;

FIG. 4 a section through the implant shown in FIG. 3;

FIG. 5 an electro-acoustic implant in accordance with the invention with an electrode carrier extending through a notch in the sound transducer;

FIG. 6 the principle of the deflection of a membrane structure such as can be used in the sound transducer in accordance with the invention;

FIG. 7 a section through membrane structures such as can be used in the sound transducer in accordance with the invention;

FIG. 8 a section through a sound transducer with a piezo layer arranged between two electrode layers;

FIG. 9 a plan view of a sound transducer with ribbon-shaped electrodes;

FIG. 10 a section through a sound transducer with ribbon-shaped electrodes arranged on the piezo layer; and FIG. 11 possible arrangements of the electro-acoustic implant in accordance with the invention in the ear.

FIG. 1 shows an electro-acoustic implant in accordance with the invention that has an elongate electrode carrier 21 and a flat sound transducer 22. The elongate electrode carrier 21 has a plurality of stimulation electrodes 23. The electrode carrier 21 can be introduced into a cochlear of a person. The flat sound transducer 22 is excitable to vibrate at least regionally by applying a voltage. The sound transducer 22 is designed such that it can be arranged in, on and/or in front of a round window or an oval window or a surgically created third window of an ear and/or can be arranged in a round window niche of an ear such that it at least partially or completely covers the corresponding window. Vibrations of the sound transducer 22 can then effect sound vibrations through the corresponding window in, on and/or in front of which the sound transducer 22 is arranged. The electrode carrier 21 extends through a surface of the flat sound transducer 22. The surface 24 is that surface by which the sound transducer covers the corresponding window at least in part when said sound transducer is arranged in front of the corresponding window.

In the example shown, the sound transducer 22 has a segmented membrane 25 as the vibrating surface 24, said segmented membrane being divided into a plurality of segments 9a, 9b, 9c through ail the layers of the membrane structure 25 by separating cutting lines 26 such that the membrane structure is mechanically decoupled at the cutting line.

FIG. 2 shows a section through the electro-acoustic implant shown in FIG. 1. The statements made on FIG. 1 therefore apply accordingly to FIG. 2. It can be recognized in the section through the sound transducer 22 that the membrane structure 25 is carried by a carrier structure 28 in the example shown. The membrane structure 25 and the carrier structure 28 are circular in the example shown and have the same radius. The carrier structure 28 has an annular surface that is spaced apart from the membrane structure 25. The annular surface is surrounded by a margin 6 that carries the membrane structure 25 at its margin. The carrier structure 28 moreover has an inner ring 27 that bounds the annular surface in the direction of its center and surrounds an opening through which the electrode carrier 21 passes through the sound transducer 22. This inner ring 27 can contact the electrode carrier 21 and can ensure that the sound transducer 22 is fixedly connected to the electrode carrier 21 or can slide on the electrode carrier such as is indicated by the double arrow 29 in FIG. 1.

FIG. 3 shows a further embodiment of an electro-acoustic implant in accordance with the present invention. An electrode carrier 21 is in turn led through a sound transducer 22, with the electrode carrier 21 carrying a plurality of electrodes 23. The sound transducer in turn has a membrane 25 that is divided into a plurality of segments 9a, 9b by cutting lines 26. The cutting lines 26 also extend radially here and sever all the layers of the membrane 25 such that the segments 9a, 9b are mechanically decoupled along the cutting line 26. The statements made on FIGS. 1 and 2 apply accordingly here.

Unlike in FIGS. 1 and 2, however, the electrode carrier 21 in FIG. 3 is led eccentrically through the sound transducer 22, i.e. at a distance greater than zero from the center of the membrane 25 of the sound transducer 22.

In the example shown, the electrode carrier 21 extends through an opening 30 in the membrane structure 25. The opening 30 and also the electrode carrier 21 have a circular cross-section, but the diameter of the electrode carrier 21 is a little smaller than the diameter of the opening 30. The sound transducer 22 is in this manner tiltable about two mutually perpendicular axes with respect to the electrode carrier 21 as is indicated by the arrows 31 and 32.

FIG. 4 shows a cross-section through an electro-acoustic implant such as is shown in FIG. 3. In the example shown in FIG. 4, the opening 30 in turn has a somewhat larger diameter than the electrode carrier 21 over the larger part of its length. The electrode carrier 2:1, however, has a spherical thickened portion 33 within the opening 30. In this respect, the diameter of the spherical thickened portion 33, that is the spherical diameter, is equal to the inner diameter of the opening 30. The opening 30 is in this respect of cylindrical design and the spherical thickened portion 33 contacts the inner cylinder wall of the opening 30. The electrode carrier 21 can hereby be tilted with respect to the sound transducer 25.

The tilt capability of the sound transducer 22 with respect to the electrode carrier 21 shown in FIG. 3 can also alternatively be achieved by a cylindrical opening 30 in that the electrode carrier 21 has a constant diameter within the opening 30 and an elastic material is arranged in the region between the inner wall of the opening 30 and the surface of the electrode carrier 21. A tilt of the electrode carrier 21 with respect to the sound transducer 23 is also hereby made possible.

FIG. 5 shows a further example embodiment of an electro-acoustic implant in accordance with the invention. The structure of this implant corresponds to that shown in FIGS. 1 to 4, but with the difference that in FIGS. 1 to 4 the electrode carrier 21 is led through the sound transducer 22 through an opening therein that is completely surrounded by the surface 24 of the sound transducer 22. In the example shown in FIG. 5, in contrast, the electrode carrier 21 is led through the sound transducer 22 through a notch 34 therein. The outer margin of the sound transducer 22 follows the concave notch 34 such that the electrode carrier 21 passes through the sound transducer 22 outside the margin, but largely within a circular surface described by the sound transducer 22. As in the other examples, the membrane 25 is also divided into a plurality of segments 9a, 9b by means of radial cutting lines 26 in FIG. 5. In the region of the notch 34, however, no segment 9a, 9b of the membrane structure 25 is provided in the example shown.

FIG. 6 shows the basic structure of a sound transducer 22 for generating sound vibrations that can be inserted into an ear. In the example shown, a membrane structure 25 that has a piezo layer 2 and two electrode layers 3 and 4 is arranged on a carrier layer 1, for example a silicon layer 1. The carrier layer 1 (elastic layer 1) can in this respect e.g. be approximately one to two times as thick as the piezoelectric layer. A voltage can be applied between the electrode layers 3 and 4 by means of a voltage source 5 or a voltage can be detected by means of a suitable detector. In the example shown, the one of the electrode layers 3 on which the piezo layer 2 is then arranged is first arranged on the carrier layer 1. The second electrode layer 4 is arranged on that side of the piezo layer 2 disposed opposite the side contacting the electrode layer 3. The electrode layers 3 and 4 can be charged with opposite polarities by application of a voltage by means of the voltage source 5 so that an electric field that passes through the piezo layer 2 arises between the electrode layers 3 and 4.

FIG. 6A shows the state of the sound transducer 22 for the event that no voltage is applied. The carrier layer 1, the piezo layer 2, and the electrode layers 3 and 4 in this respect extend in one plane, that is are flat. If now, as shown in FIG. 6B, a voltage is applied between the electrode layers 3 and 4 by means of the voltage source 5, an electric field passes through the piezo layer 2. The piezo layer 2 is hereby shortened, whereby the total membrane structure 25 of the carrier layer 1, of the electrode layers 3 and 4, and of the piezo layer bends upward in the direction of the piezo layer.

If the polarization of the voltage 5 is reversed, the piezo layer 2 expands and the membrane structure bends away from the piezo layer 2. If an alternating voltage is applied at the voltage source 5, the membrane structure can be set into vibration.

FIG. 7 shows two possible embodiments of the sound transducer 22 in accordance with the invention in comparison. The embodiment shown in FIG. 7A corresponds to that shown in FIG. 6 where the membrane structure is divided into segments 9a, 9b. In the embodiment shown in FIG. 7B, in contrast, a non-segmented membrane structure 25 is present. The segmented embodiment shown in FIG. 7A in this respect enables a higher deflection in this respect with regard to the unstructured membrane shown in FIG. 7B since the two elements 9a, 9b can freely deform at the center 8 of the circular membrane and therefore undergo a constant curvature in only one direction in the direction of the margin 6 toward the center 8, The deflection at the center 8 is smaller in the unsegrnented membrane shown in FIG. 7B. Furthermore, the curvature of the membrane varies from the margin 6 in the direction of the center 8 and changes its sign. On the other hand, FIG. 78 in contrast facilitates a gas-tight and a fluid-tight termination of an opening through the sound transducer in accordance with the invention.

FIG. 8 shows a section through a sound transducer 22 in accordance with the invention in which a piezoelectric layer 2 is arranged between an electrode layer 3 and an electrode layer 4. The embodiment substantially corresponds to that shown in FIG. 6. A voltage that causes an electric field 10 passing through the piezoelectric layer 2, as can be recognized in the magnification, can be applied between the electrode layers 3 and 4 by means of a voltage source 5. The electric field 10 has the effect that the piezo layer 2 expands or contracts, whereby the membrane structure bends with the carrier layer 1, with the electrode layers 3 and 4, and with the piezo layer 2. If an alternating voltage is applied at the voltage source 5, the membrane structure can be set into vibration.

FIG. 9 shows a plan view of a sound transducer 22 in accordance with the invention in which the electrodes are arranged as in FIG. 10. The electrodes extend over the surface shown in the embodiment of FIG. 10. Further electrodes 3 and 4 can also preferably be arranged within the piezoelectric layer beneath the shown electrodes 3 and 4. The electrodes 3 and 4 then pass through the piezoelectric layer 2 in one or more planes.

The membrane 25 shown in FIG. 9 is in turn circular and the electrodes are designed as concentric circle sections. In this respect, a plurality of electrodes 3 and 4 extend in a circular manner around the center 8 of the membrane, with the polarity of the electrodes 3 and 4 changing from the margin 6 in the direction toward the center 8. The membrane shown in FIG. 9 is segmented in eight segments 9a, 9b that are fixedly arranged at a common margin 6 and are mechanically decoupled with respect to one another.

The plurality of electrodes 3 and 4 are contacted in the example shown in FIG. 9 by conductors 11 and 12 that extend radially from the margin 6 in the direction of the center 8. In this respect, electrodes of one polarity 3 are always contacted by a conductor 11 and electrodes of the other polarity 4 by another conductor 12, A plurality of electrodes 3 of the same polarity are therefore always contactable by a common conductor 11.

It can be recognized that the electrodes of the one polarity 4 and those of the other polarity 3 engage into one another in the manner of a comb and are together contacted at their one end by common conductor 11 or 12 respectively. The electrodes of one polarity 4 in this respect extend from their common conductor 12 in the direction of the conductor 11 of the other polarity, but end before they reach it so that no electric contact is established between electrodes 4 of one polarity and a conductor 11 of the other polarity. Electrodes 3 and 4 always extend alternatingly in the radial direction in the larger part of the region between two conductors 11 and 12 of different polarities so that electric fields can form between the electrodes, as shown above, that pass through the piezo layer and can hereby effect an extension or contraction of the piezo layer 2.

FIG. 10 shows a further embodiment of the sound transducer 22. The embodiment shown in FIG. 10 can also be a section through the embodiment shown in FIG. 9. In this respect, a piezo layer 2 that directly contacts the carrier layer 1 in the example shown is arranged on a carrier layer 1. Ribbon-shaped electrodes 3, 4 having alternating polarity are now arranged next to and in parallel with one another on the side of the piezo layer 2 remote from the carrier layer 1. Electrodes of the one polarity 3 therefore alternate with the electrodes of the other polarity 4 in cut-away view on the surface of the piezo layer 2 remote from the carrier layer 1. In the cut-away view in FIG. 6, the ribbon-shaped electrodes 3 and 4 are also shown in section and here have a substantially rectangular cross-section. The electrodes 3 and 4 are equidistant from one another.

An electric field 10 is now formed between two respective adjacent electrodes 3 and 4 that extends from one of the electrodes 3 through the piezo layer 2 to the adjacent electrode of opposite polarity 4. The electric field 10 that arises by applying a voltage to the voltage source 5 between the electrodes 3 and 4 therefore passes through the piezo layer 2. The latter thereby changes its length so that the membrane structure bends upwardly or downwardly with the carrier layer 1 and the piezo layer 2. As also in the preceding examples, the membrane structure can be carried by a frame 6 and can be segmented or contiguous.

FIG. 11 shows in part Figures A, B, C and D how the electro-acoustic implant in accordance with the invention is implantable in the ear of a person. In this respect, the sound transducer 22 is arranged in front of the round window in part FIGS. 11A and 11B, while it is arranged before an artificially created third window in part FIGS. 11C and 11D. In all the part Figures, the electrode carrier 21 extends through the sound transducer 22 into the cochlea.

In part FIGS. 11A and 11C, the electrode carrier 21 passes centrally through the sound transducer 22, as shown in FIGS. 1 and 2. In part FIGS. 11B and 11D, the electrode carrier 21 extends eccentrically through the sound transducer 22, as shown in FIGS. 3 and 4.

The electrode carrier 21 can have a contact 35 toward the outside so that an energy supply for the implant and a power supply can be accommodated outside.

The lead 35 can extend through a surgically created opening in the mastoid (part of the temporal bone). The partial removal of the mastoid is called a "mastoidectomy" and is part of the standard procedure for implanting a CI.

The invention claimed is:

1. An electro-acoustic implant, comprising
   an elongate electrode carrier having a plurality of stimulation electrodes configured to be introduced into a cochlea of a human subject; and
   a flat sound transducer that is excitable to vibrate at least regionally by applying a voltage,
   wherein:
      the sound transducer is configured to fit in, on, and/or in front of a round window or an oval window or a surgically created third window of an ear and/or in a round window niche of an ear, covering the corresponding window at least partially or completely, so that vibrations of the sound transducer effect sound vibrations through the corresponding window;

the elongate electrode carrier extends through a plane of the flat sound transducer that extends, when the sound transducer is arranged in front of the corresponding window, at least partially over the corresponding window;

the elongate electrode carrier pierces the plane of the flat sound transducer;

the flat transducer has a membrane structure as a part of its plane;

the membrane structure has at least one carrier layer and at least one piezo layer that is arranged on the carrier layer and that comprises a piezoelectric material so that the sound transducer is excitable to vibrate at least regionally by applying the voltage to the piezo layer; and the membrane structure in the plane is divided by at least one cutting line separating all the layers of the membrane structure into at least two or more segments so that the membrane structure is mechanically decoupled at the cutting line.

2. The electro-acoustic implant of claim 1, wherein the sound transducer is fixable in the middle ear so that its vibration is transferable to a fluid in the cochlea.

3. The electro-acoustic implant of claim 1, wherein the elongate electrode carrier extends through a center of the plane of the flat sound transducer.

4. The electro-acoustic implant of claim 1, wherein the elongate electrode carrier extends eccentrically through the plane of the flat sound transducer.

5. The electro-acoustic implant of claim 1, wherein the elongate electrode carrier extends through the flat sound transducer through a notch at the edge of the plane thereof.

6. The electro-acoustic implant of claim 1, wherein the elongate electrode carrier is a cochlea implant electrode whose length is so that only frequencies larger than or equal to 1000 Hz are excitable by the cochlea implant electrode in the implanted state.

7. The electro-acoustic implant of claim 1, wherein the sound transducer is displaceable with respect to the electrode carrier in a longitudinal direction of the electrode carrier.

8. The electro-acoustic implant of claim 1, wherein the sound transducer is tiltable with respect to the electrode carrier, with the sound transducer and the electrode carrier being connected to one another via a joint.

9. The electro-acoustic implant of claim 1, wherein the electrode carrier extends through an opening in the plane of the sound transducer, the opening having a diameter that is larger than a diameter of the electrode carrier so that the electrode carrier is at least regionally spaced apart from a wall of the opening.

10. The electro-acoustic of claim 9, wherein the elongate electrode carrier is a cochlea implant electrode whose length is so that only frequencies larger than or equal to 1000 Hz are excitable by the cochlea implant electrode in the implanted state.

11. The electro-acoustic implant of claim 10, wherein the sound transducer is tiltable with respect to the electrode carrier, with the sound transducer and the electrode carrier being connected to one another via a ball joint.

12. An electro-acoustic implant, comprising
an elongate electrode carrier having a plurality of stimulation electrodes that configured to be introduced into a cochlea of a human subject; and
a flat sound transducer that is excitable to vibrate at least regionally by applying a voltage,
wherein:
the sound transducer is fixable in the middle ear so that its vibration is transferable to a fluid in the cochlea,
the flat transducer has a membrane structure as a part of its plane,
the membrane structure has at least one carrier layer and at least one piezo layer that is arranged on the carrier layer and that comprises a piezoelectric material so that the sound transducer is excitable to vibrate at least regionally by applying the voltage to the piezo layer,
the membrane structure in the plane is divided by at least one cutting line separating all the layers of the membrane structure into at least two or more segments so that the membrane structure is mechanically decoupled at the cutting line,
the sound transducer is configured to fit in, on, and/or in front of a round window or an oval window or a surgically created third window of an ear and/or in a round window niche of an ear, covering the corresponding window at least partially or completely, so that vibrations of the sound transducer effect sound vibrations through the corresponding window;
the elongate electrode carrier extends through the plane of the flat sound transducer that extends, when the sound transducer is arranged in front of the corresponding window, at least partially over the corresponding window, and
the elongate electrode carrier pierces the plane of the flat sound transducer.

13. The electro-acoustic implant of claim 12, wherein the elongate electrode carrier extends through the flat sound transducer through a notch at the edge of the plane thereof.

14. The electro-acoustic of claim 12, wherein the elongate electrode carrier is a cochlea implant electrode whose length is so that only frequencies larger than or equal to 1000 Hz are excitable by the cochlea implant electrode in the implanted state.

15. The electro-acoustic implant of claim 12, wherein the sound transducer is displaceable with respect to the electrode carrier in a longitudinal direction of the electrode carrier.

16. The electro-acoustic implant of claim 12, wherein the sound transducer is tiltable with respect to the electrode carrier, with the sound transducer and the electrode carrier being connected to one another via a joint.

17. The electro-acoustic implant of claim 16, wherein the sound transducer is tiltable with respect to the electrode carrier, with the sound transducer and the electrode carrier being connected to one another via a ball joint.

18. The electro-acoustic implant of claim 12, wherein the electrode carrier extends through an opening in the plane of the sound transducer, the opening having a diameter that is larger than a diameter of the electrode carrier so that the electrode carrier is at least regionally spaced apart from a wall of the opening.

* * * * *